United States Patent [19]
Adams et al.

[11] Patent Number: 5,304,209
[45] Date of Patent: Apr. 19, 1994

[54] REMOTE-CONTROL TEMPORARY PACEMAKER

[75] Inventors: Theodore P. Adams, Edina; Gene M. Berghoff, Eden Prairie; Scott T. Latterell, Minneapolis, all of Minn.

[73] Assignee: Angeion Corporation, Plymouth, Minn.

[21] Appl. No.: 764,626

[22] Filed: Sep. 24, 1991

[51] Int. Cl.$^5$ ............................. A61N 1/372
[52] U.S. Cl. ........................ 607/30; 607/32; 607/36; 607/10; 128/903
[58] Field of Search .......... 128/903, 419 PG, 419 PS, 128/419 PT, 384, 419 P; 607/30, 32, 36, 10

[56] References Cited

U.S. PATENT DOCUMENTS

| | | | |
|---|---|---|---|
| 4,124,031 | 11/1978 | Mensink et al. | 128/419 PG |
| 4,432,363 | 2/1984 | Kakegawa | 128/419 PS |
| 4,907,593 | 3/1990 | Rapach et al. | 128/419 PG |
| 4,958,632 | 9/1990 | Duggan | 128/419 PG |
| 5,095,903 | 3/1992 | DeBellis | 128/903 |
| 5,113,869 | 5/1992 | Nappholz et al. | 128/903 |

FOREIGN PATENT DOCUMENTS 8207533  11/1983  France ................ 128/419 PG

OTHER PUBLICATIONS

Webster's Third New International Dictonary, Gove, editor, Merriam Co. 1971, p. 2047.

Primary Examiner—William E. Kamm
Assistant Examiner—George Manuel
Attorney, Agent, or Firm—Patterson & Keough

[57] ABSTRACT

A temporary pacemaker combines technologies of the implantable pacemaker, the waterproof watch, with a separate remote-control programming unit that communicates with the pacemaker via IR radiation. An LCD readout on the temporary pacemaker continuously reports on current settings, and is monitored periodically, as well as during the setting process. The programming unit is aimed at an IR sensor on the pacemaker, and its dedicated controls are used for setting, with the aid of prompting messages on its own LCD panel. Battery life is about 6-9 months, while that for the lithium battery in the sealed and sterilizable pacemaker approaches five years.

11 Claims, 7 Drawing Sheets

REMOTE-CONTROL TEMPORARY PACEMAKER

BACKGROUND OF THE INVENTION

1. Field of the Invention

The present invention relates to temporary pacemakers, also known as wearable external pacemakers, and more particularly pertains to an external pacemaker that is VELCRO strapped to a patient's arm, chest or another portion of the body, using VELCRO or some other means.

2. Description of the Prior Art

There are several varieties of prior art pacemakers that are placed outside the body to be used temporarily while a patient is awaiting implantation of a permanent pacemaker or post-operative use. To use a prior art pacemaker, it is customary to connect a heart wire (hereinafter frequently designated as a lead) through the open chest and connect it to the heart or inserting a disposable lead transcutaneously, inserting it through a vein and into the heart. The external end of the lead or heart wire is, of course, attached to the pacemaker unit, so it follows that the unit must be positioned close to the patient. This is the first primary requirement of a temporary pacemaker.

External pacemakers of the prior art intended f or temporary use by new patients have been too bulky to be worn conveniently on the patient's body. In many instances, an extension cable is used between the lead or heart wire and the external pacemaker so that the pacemaker can be placed on an IV pole. As a result, the patient has been uncomfortably constrained by being connected by lead, heart wire, or cable to a comparatively immobile instrument. Added is the mental distress of knowing that even normal motion may dislodge the lead or heart wire with potentially hazardous results. Large control components—usually rotary switches and keyboards—are employed to make it easy for medical personnel to set pacing variables, but these also invite tampering by patient or visitors to the patient's room. Further, such components prevent adequate sterilization of the pacemaker before its use by a different patient. Added is the custom of using short-lived batteries, requiring routine instrument maintenance that sometimes is forgotten under stress, especially since personnel expected to perform it are unfamiliar with such procedures.

The second primary requirement is that a temporary pacemaker must be easily and readily adjustable. This must be done immediately after connection to the patient, and on some occasions, must be done on an emergency basis during the first crucial hours of a patient's experience with the pacemaker. Because of this requirement, the necessary controls are made relatively large and easy to manipulate. Usually, programming is accomplished by means of push buttons and rotary switches placed on one face of the enclosure. The same f ace of the box or enclosure must also support one or more readout displays as well. As a result of these combined factors, the temporary pacemaker is much larger than an implantable pacemaker.

These two requirements—proximity to the patient and ready programmability—lead to a series of design conflicts that have not been resolved in the prior art to date. The present invention, however, resolves all of them. The nature of these design conflicts can be appreciated from the following descriptions:

First, one would prefer to attach the temporary pacemaker (hereinafter frequently designated as a unit) to the patient's body, to avoid inadvertent tension on the lead or heart wire. Ideally, it would be attached to the patient's upper arm, chest, or leg using a snug but comfortable strap. Prior art units are much too large to make such a practice convenient or comfortable, however. As a result, the comparatively bulky unit is sometimes tied to the patient's bed, hung on an IV pole, or placed on a nearby table, with a connecting cable provided. With such arrangements, the patient is often unable to move in bed without the hazard of dislodging the lead, a fact that adds mental stress to physical discomfort. In other instances, especially for ambulatory patients, the unit is sometimes pinned to the patient's clothing. All of these arrangements require a longer lead than would a body-mounted unit, though, and both lead length and the relative immobility of the unit increase the possibility of accidentally stressing the lead or heart wire.

The second kind of conflict arises because having a readily adjustable unit situated very near the patient opens the possibility of tampering with the control settings by the patient or visitors. Experience shows that this is a genuine concern, even though it may seem at first to be an implausible one. Remedial changes, both in design and of an ad hoc kind, have proven unsatisfactory. A cover or interlock on the controls has been provided in some cases. But this places an extra burden on medical personnel, who must quickly release the lock, sometimes under stressful conditions. The same is true of interlock arrangements that must be negotiated before settings can be changed. When an unlocked cover is provided, medical personnel have been known to put tape over the cover to make it harder for the patient or visitors to change settings. But this is obviously an unsatisfactory solution, since time-consuming tape removal is a handicap, especially in emergencies, and also the presence of the tape interferes with vision in routine monitoring of the unit.

The third conflict arises because the unit is close to the patient and blood contact is inevitable in the use of the overall system. Therefore, a means of disinfecting the unit is called for by standards of sound medical practice before the same unit is used for a different patient, in spite of the fact that the lead used with the unit is disposable. Such standard practice in this case is augmented by widespread public anxiety concerning HIV infection and AIDS, where human blood is concerned. The units are much too expensive for casual disposal because they are relatively complex and are manufactured in small volumes. But these units are not sealed, so that disinfecting liquids cannot easily and effectively be used. The components cannot withstand temperatures even approaching autoclave temperatures. Furthermore, gas sterilization, although used, is unsatisfactory because literally days are required for "aeration", or permitting the toxic sterilizing gases to diffuse out of the many interstices inside the case.

A fourth shortcoming common to all prior art temporary pacemakers is unrelated to the conflicting requirements just cited. It is customary to employ comparatively short-lived batteries to power the unit, with the expectation that the batteries will be checked and usually changed for each new patient. But on occasion this routine step has been neglected with serious consequences. Longer-lived batteries are available, but are most compatible with smaller and more efficient systems.

The present invention resolves all of the conflicts just outlined. The essential innovation places the bulky control mechanisms in a unit that is separate and that never comes in contact with the patient. By means of infrared radiation, the temporary pacemaker communicates with a small, sealed unit worn by the patient. This resolves the tampering issue, the comfort and convenience issue, and the sterilization issue. In addition, the new, wearable unit of the invention is a natural recipient o.f a long-lived battery.

SUMMARY OF THE INVENTION

The general purpose of the present invention is to provide a temporary (or external) pacemaker that resolves the conflicts common to all those of the prior art. It is small, comfortable, tamper-proof, easy to use and monitor, long-lived, safe and sterilizable. The unit worn by the patient employs the combined technologies of the waterproof watch and the implantable pacemaker. The temporary pacemaker is free of all external controls. It incorporates a sealed jack (long a standard component) into which the lead is plugged. The disposable lead is specially designed, including a mechanical connector and shortened length lead f or the unit of this invention, and is a major accessory. When using a generic lead or heart wire, a specifically designed connector block is used. The temporary pacemaker unit is worn like a wrist watch, but typically on the upper arm, chest, or leg of the patient, with a disposable strap serving as band, the strap having VELCRO or similar fastening.

According to one embodiment of the present invention, there is provided a wearable temporary pacemaker resembling an implantable pacemaker in shape and size, but differs in that it has an LCD display array clearly visible at its outer face. These displays require extremely small amounts of power, so that the life of the primary lithium battery in the pacemaking unit of this invention will approximate that of a battery in an implanted pacemaker, which is about five years. The LCD array continuously displays variables sensed, as well as the last-set values of the pacing variables. The unit can easily be sterilized by disinfecting liquid and/or gas sterilization after the conclusion of one patient's wearing.

The wearable temporary pacemaker is accompanied by a hand-held remote-control programmer. The programmer is of convenient size, probably about the size of a pack of cigarettes, and can be stored conveniently, but out of the patient's reach. The programmer includes an LCD readout and programming buttons including a stat button which automatically transmits a set of predetermined values for all functions of the temporary pacemaker unit. The programmer incorporates an LCD display that presents parameters and values, and a keyboard with dedicated keys for setting each pacing variable. Because of intermittent use, its battery will last for approximately a 6-9 months. The programming unit communicates with the wearable temporary pacemaker unit by means of electromagnetic radiation, directed at a sensor located behind a window on the latter, and without physical contact of the two units. It is possible to use visible light, RF, or IR radiation, but the last is preferred. Ambient light can cause problems in the first case. The RF option has the shortcoming that it is less directional than the other two, and use of the programmer for one patient could inadvertently affect the setting of another patient's wearable unit.

Significant aspects and features of the present invention include a temporary (external) pacemaking unit that has no controls and is sealed like a waterproof watch or implantable pacemaker.

Another significant aspect and feature of the present invention is the temporary pacemaker unit's small size, which permits the patient to wear it comfortably attached to the upper arm, chest or other part of the body, while affording the patient maximum freedom of motion without hazard to unit or lead, and with reduced mental anguish from fear of accidentally dislodging the lead.

Still another significant aspect and feature of the present invention is a disposable band for attachment of the unit to the patient, the band having a VELCRO or other convenient fastener.

Yet another significant aspect and feature of the present invention is a readout display using LCD technology on the exposed face of the temporary pacemaker unit presenting continuously the most recent setting of each pacing variable, as well as real-time pace and sense indications, and a battery-condition indication.

Another significant aspect and feature of the present invention is a disposable lead to be used for one patient only that plugs into a sealed jack in the pacemaker unit. This lead is designed differently than a standard lead, such that it is shorter to make it safer and more comfortable for the patient. It also has a safer mechanical connector to prevent the lead from disconnecting.

Another significant aspect and feature of the present invention is a connector block/adapter to be used when connecting a heart wire or generic lead to the heart. This adapter is designed for a safer mechanical connection to the unit and to allow the use of a generic lead or heart wire.

Another significant aspect and feature of the present invention is a primary lithium battery that powers the temporary unit, giving it a life of the order of five years.

Still another significant aspect and feature of the present invention is a remote-control programming unit that never makes physical contact with the wearable temporary pacemaker unit or patient, that has large and easy-to-use control elements on it, as well as a display presenting prompting messages, and that communicates with the temporary unit by means of IR radiation, or in the alternative, RF radiation.

Other significant aspects and features of the present invention is a remote-control programming unit that incorporates automatic shut-off.

Having thus described embodiments and features of the present invention, it is a principal object of the invention to provide a temporary pacemaker of relatively long life, and having no need for routine maintenance such as battery changing.

One object of the present invention is to provide a temporary pacemaker that can be immersed in liquid disinfectant for improved sterilization after use by each patient, or gas sterilization, thus preparing it for use with a further patient.

Another object of the present invention is tamper-proof by virtue of having no external controls to be manipulated by unauthorized persons, such as visitors, or the patient himself or herself.

A further object of the present invention is to provide a temporary pacemaker that is continuously ready for programming, without any time delays caused by unlocking, interlock disabling, or removal of improvised barriers to access.

Still another object of the present invention is to provide localized, noise-immune, reliable communication from unit to unit by IR radiation.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the FIGURES thereof and wherein.

PIG. 3 illustrates a front view of the remote control programmer.

DESCRIPTION OF THE PREFERRED EMBODIMENTS

Figure 1:
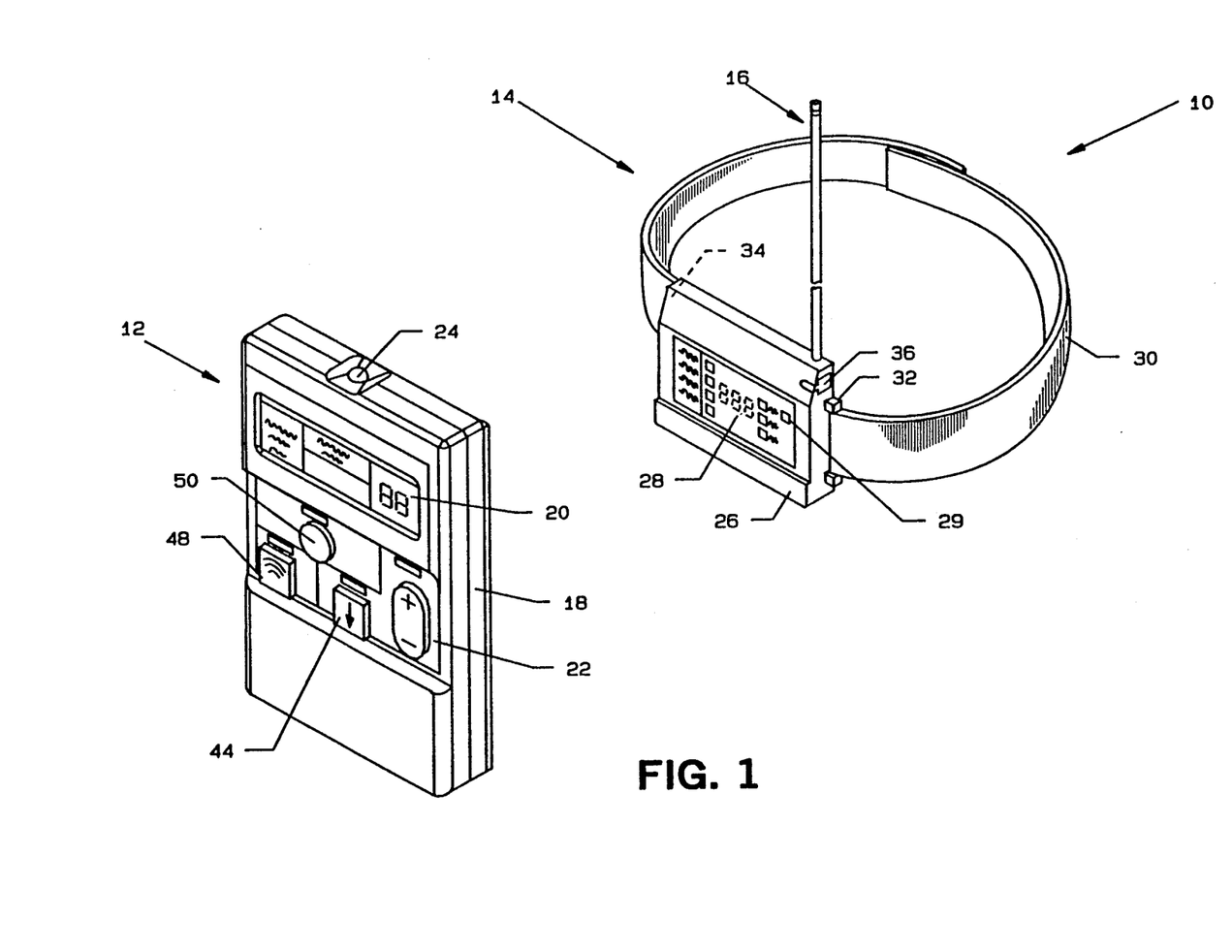
FIG. 1 illustrates a perspective view of a remote control temporary pacemaker.

FIG. 1 illustrates a perspective view of the remote control temporary pacemaker system 10 including a hand-held remote programmer 12, a temporary pacemaker 14 and a lead 16 secured to the temporary pacemaker 14. The remote programmer 12 includes a case 18, an LCD 20, a control panel 22 and an infrared source 24 through which data is sent to program the temporary pacemaker 14.

The temporary pacemaker 14 includes a water-proof, hermetically sealed case 26, an LCD panel 28, an IR Sensing window 29 to communicate with the programmer 12, a disposable strap 30 of suitable length made of VELCRO or other suitable material attached to the case 26 about mounting posts 32 and 34 at opposing ends of the case 26. The lead 16 attaches to the temporary pacemaker 14 by a connector block 36. The disposable strap 30 can be of a length suitable for wearing of the temporary pacemaker 14 about the arm of a patient, or in the alternative, can be of a greater length for wearing of the temporary pacemaker 14 about the chest of a patient when the lead 16 is a heart wire exiting the body through the chest wall or even to the leg of the patient.

Figure 2:
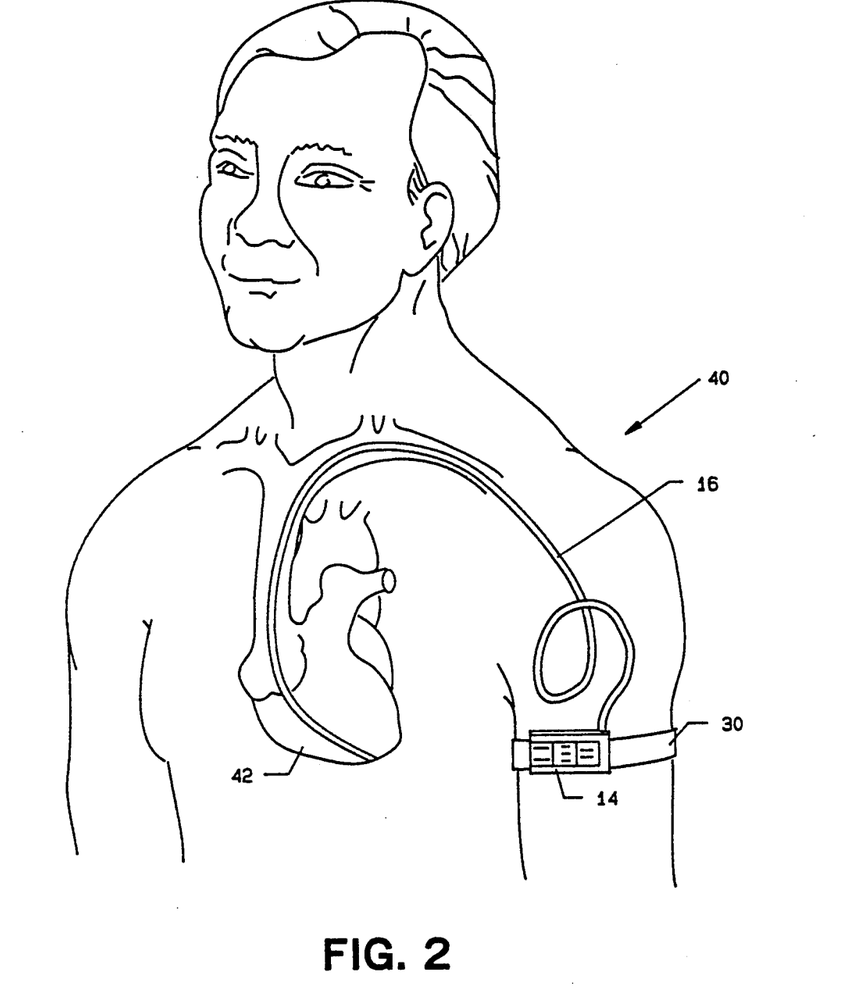
FIG. 2 illustrates a patient wearing the temporary pacemaker.

FIG. 2 illustrates a patient 40 wearing the temporary pacemaker 14 of the present invention attached to the patient's arm by the disposable strap 30, and fitted to a lead 16 that is introduced transcutaneously into the patient's heart 42.

Figure 3:
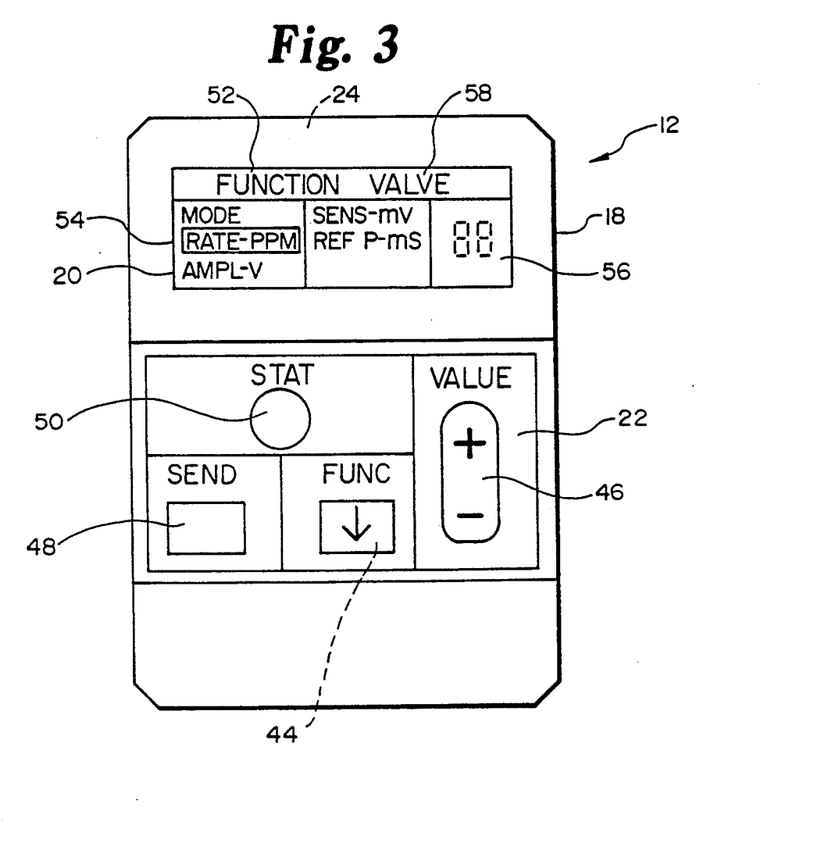
Figure 4:
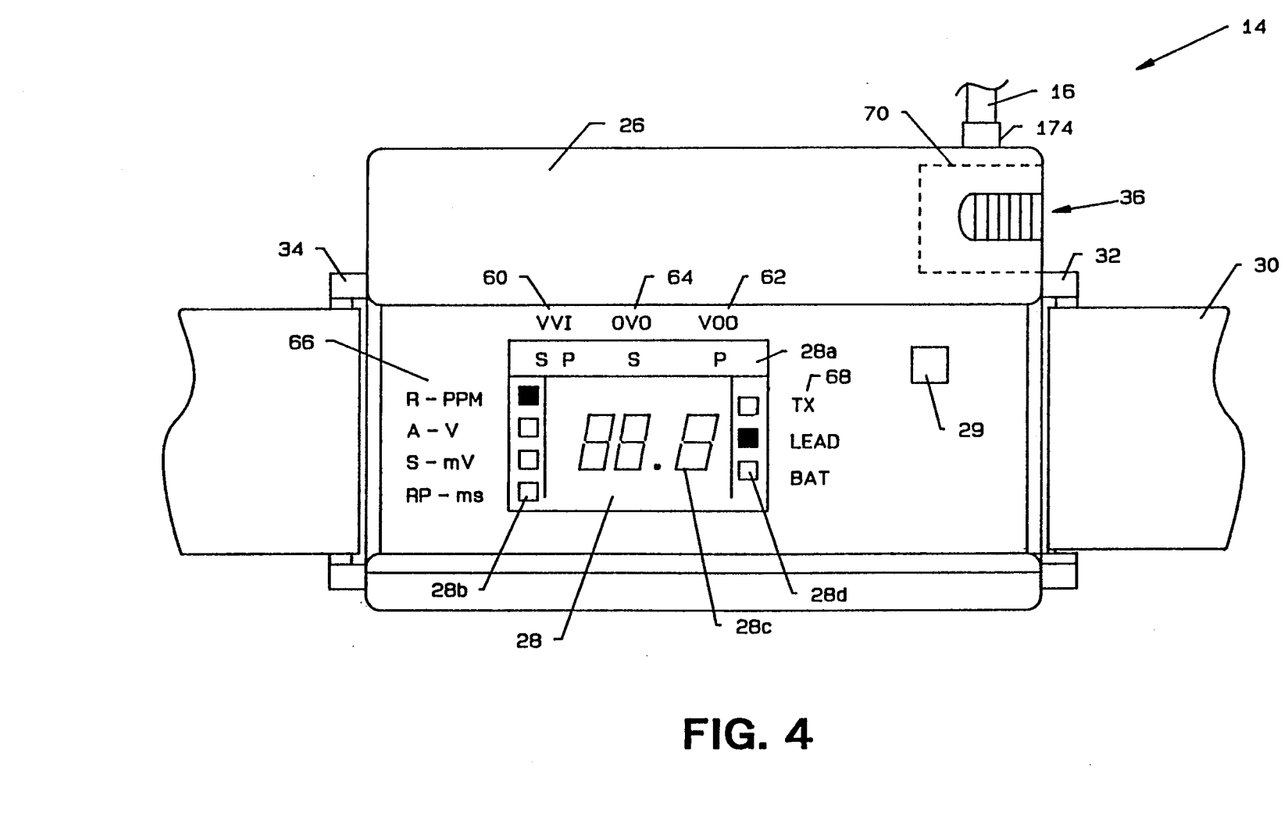
FIG. 4 illustrates a front view of the temporary pacemaker.

FIG. 3 illustrates the remote programmer 12 of the present invention, having keys 44, 46, 48 and 50 in a control panel 22 for setting pacing variables whose values can be read on the temporary pacemaker 14 of FIG. 4, and having an LCD 20 for presenting prompting messages that relate to data to be transmitted to the temporary pacemaker 14 of the present invention. Key 44 is a function key, key 46 is a value key, key 48 is a send (or enter) key and key 50 is a stat key.

Pressing any key 44 through 50 will turn the remote programmer 12 on. If the STAT key 50 is hit, it will also transmit all of the STAT settings as well as turn the unit on. The remote programmer 12 will always come on in the nominal settings. These settings are parameter values predetermined by the manufacturer as the norm for external, single chamber pacing. Whereas the STAT settings are emergency settings. The remote programmer 12 will turn off automatically if there have been no key strokes for 60 seconds.

Pressing the "FUNCTION" key 44 scrolls forward through the five programmable functions under the function column 52. The function key 44 allows the user to scroll and cycle down through the functions in only one direction. The function chosen will always be highlighted by an outlined square 54 around that function. Pressing the "VALUE" key 46 scrolls through the values for the function selected by the value key 44. The current value 56 will always be displayed on the right side of the LCD 20 under the value heading 58. When the mode function is chosen, all three mode options (VVI, OVO, VOO) will appear under the function column 52 with an underline beneath the mode currently selected. The parameter values will appear one at a time under the value heading 58. Functions/values for the various five programmable functions are as follows:

Modes:
(VVI, OVO, VOO)—mode options will scroll left to right.

Parameters:
Rate (50-150 PPM incrementing 1 PPM<100 and 5 PPM>100, utilizing two ramping speeds).
Amplitude (0.5-8 volts incrementing 0.5 volts).
Sensitivity (0.5mV, 1.0mv, −10mv incrementing 1mv, 10–20mV incrementing 2mV).
Refractory Period (150–400ms incrementing 50ms)

Pressing the "SEND" key 48 transmits the desired function to the temporary pacemaker 14. Only one function can be sent at a time unless using the STAT key. The function being sent must be displayed on the remote programmer 12 at the time it is being transmitted and the programmer should be within 30 inches of the temporary pacemaker 14. The data is transmitted via infrared light pulses generated at the infrared source 24 and received by the temporary pacemaker 14.

Pressing the "STAT" key 50 at any time will automatically transmit a set of predetermined values of all the functions to the temporary pacemaker 14. Stat values are: Mode - VVI, Rate - 7OPPM, Amplitude volts - 8 volts sensitivity - 2.0 mv, and refractory period - 3OOms.

When the remote programmer 12 battery voltage falls below the minimum specified voltage, the LCD 20 will flash the "OW BAT-PRGRMR" message. it Will appear centered under the value heading 58, toward the bottom of the LCD 20. The remote programmer 12 uses one 6V lithium magnesium dioxide battery.

FIG. 4 illustrates a front view of the temporary pacemaker 14 where all numerals correspond to those elements previously described. The temporary pacemaker 14 can never be turned off completely. It is always programmed at its previous programmed settings and will either be pacing or sensing. If in the VVI mode 60, the temporary pacemaker 14 will sense, and pace only on demand. In the VOO Mode 62, the temporary pacemaker 14 will pace continuously, and in the OVO mode 64, the temporary pacemaker 14 will only sense and will always be in operation. The other functions of the temporary pacemaker will always continue to be displayed with the reference to column 66 on the LCD panel 28. The mode of operation VVI 60, VOO 62, or OVO 64 is selected/programmed via the remote programmer 12.

The status of all functions will be displayed at all times. The mode status 60, 62 or 64 will be indicated by a small alphanumeric indicator, "P" for pace and "S" for sense beneath the selected mode in the LCD subdisplay 28a. Another indicator subdisplay 28b will continuously scroll next to a graphic representation of each parameter shown in column 66 stopping 1½ seconds by each one. As the parameter indicator changes with reference to column 66, a number will appear in the numeric display 28c of the LCD panel 28 which represents the value of the parameter of column 66 being highlighted. LEAD (open lead), BAT (low battery), and TX (transmit error) signals will be displayed via a flashing indicator mark in subdisplay 28d adjacent to column 68 only when they occur.

It is recommended that the user program a patient's temporary pacemaker 14 for the first time prior to connecting it to the patient. This will reassure that the patient receives the correct patient values. The temporary pacemaker 14 only receives one function at a time from the remote programmer 12. The data is transmitted via infrared light pulses from the remote programmer 12 which requires the remote programmer 12 to be within 36 inches of the temporary pacemaker 14. As a check, the temporary pacemaker 14 LCD 28 will display the data upon receiving it. The preprogrammed unit, programmed in the ovo position, is then connected to the patient. At this time, the temporary pacemaker 14 is activated by selecting the appropriate pacing mode VVI 60 or VOO 62. After initial programming/setup has been completed, a function can be reprogrammed at any time without disconnecting the temporary pacemaker 14 or shutting it off.

When the stat key 50 is pressed on the remote programmer 12, the programmer 12 automatically transmits a set of predetermined values mode - VVI, rate - 70 PPM, Amplitude - 8 volts, sensitivity - 2.0 mV, refractory period - 300 Ms of all the functions to the temporary pacemaker 14. Use of the "send" key 48 is not required when transmitting one STAT value.

With the use of a disposable patient belt or arm strap, the device can be positioned on the arm, chest, leg or another part of the body. The pulse generator is designed to be used with a custom or stock lead, or a heart wire. An adapter must be used if using a stock lead or a heart wire. The unit shall be protected from potential damage caused by a defibrillator.

Figure 6:
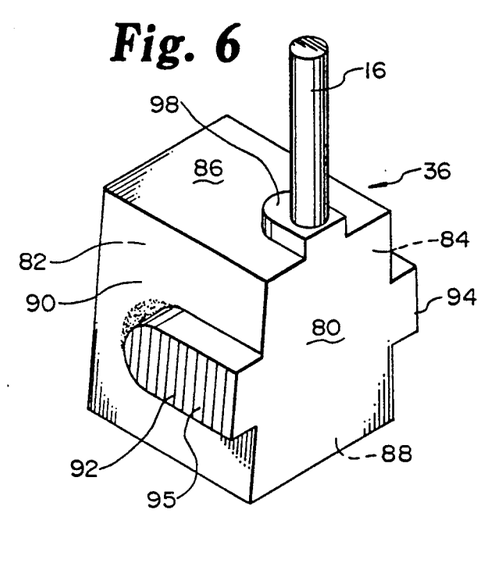
FIG. 6 illustrates a perspective view of a connector block with a lead.
Figure 7:
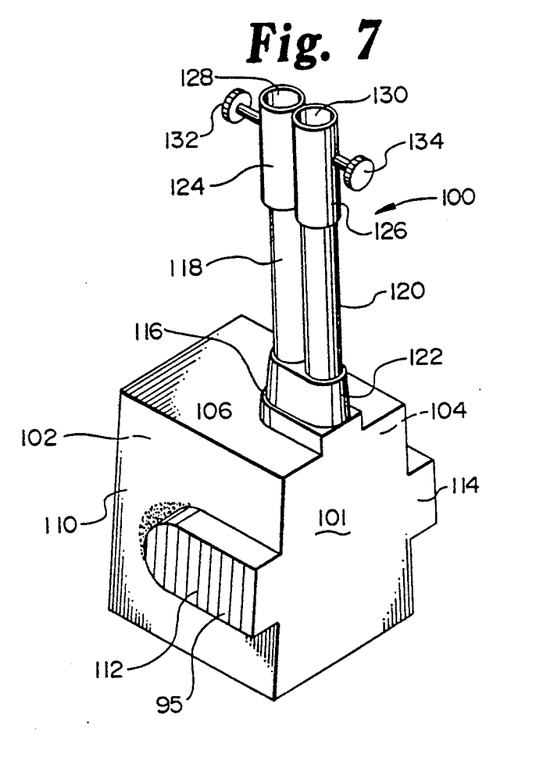
FIG. 7 illustrates a perspective view of a connector block for use with generic leads.

A connector block 36 as illustrated in FIG. 6 aligns in a cavity 70 in the upper right portion of the case 26 to make electrical contact between the temporary pacemaker 14 and the custom lead 16. An adapter connector block 100 illustrated in FIG. 7 is provided should connection to a generic lead or heart wire be required. The temporary pacemaker 14 is also protected from potential damage which could be caused by a defibrillator.

Figure 5:
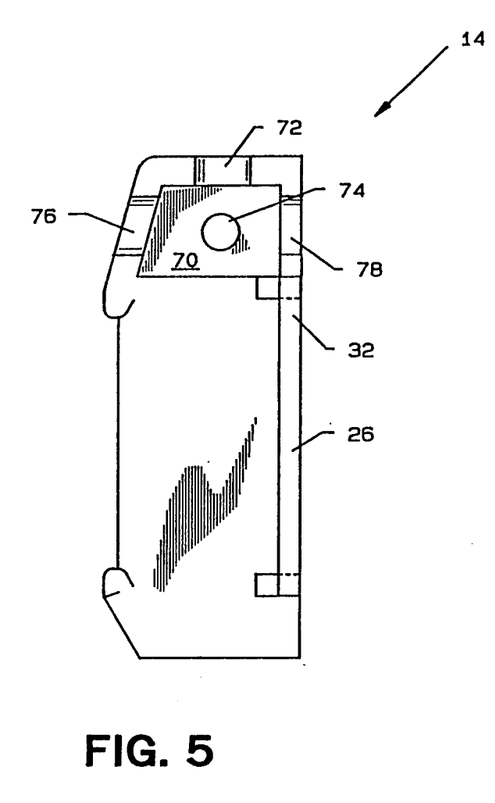
FIG. 5 illustrates an end view of the temporary pacemaker.

FIG. 5 illustrates a right end view of the temporary pacemaker 14 where all numerals correspond to those elements previously described. Illustrated in particular is the connector cavity 70 in the general shape of a quadrilateral having three sides which are either vertical or horizontal and a fourth side which is oblique with references to the other side walls. The unique shape of the cavity 70 allows only for proper orientation of the connector block 36 causing the lead 16 of FIG. 4 to extend vertically through a slotted hole 72 at the top of the cavity 70. A multicircuit connector pin 74 extends toward the viewer of FIG. 5 for contacting the appropriate internal lead contactors of the connector blocks 36 or 100 of the following FIGS. Alignment slots 76 and 78 on the front and back of the case 26 allow for alignment with corresponding alignment tabs on the connector block 36 as described in the following FIGS. The lead connector offers protection against inadvertent lead pullout from the temporary pacemaker 12, where previous art connectors were often only pins engaged straight way into holes in a simple connector arrangement. The connector block 36 is inserted sideways (to the left) into the cavity 70 and snaps into place. Vertical pull on the lead 16 with subsequent disconnect is very unlikely in that the connector 36 will only disconnect with sideways movement of the right and not with vertical movement. The snap fit of the connector block 36 also discourages removal by inadvertent means.

FIG. 6 illustrates a perspective view of the connector block 36 where all numerals correspond to those elements previously described. Opposing end surfaces 80 and 82 and surface 84 are vertical surfaces while surfaces 86 and 88 are horizontal surfaces. Surface 90 is in oblique alignment with the other surfaces 80-88. Alignment tabs 92 and 94 extend from surfaces 90 and 84, respectively, for alignment with alignment slots 76 and 78 of the case 26. Optional finger grips 95 can be provided to provide for insertion and removal. A colored area or graphic area can also be provided to visually alert a user that the connector block 36 is not completely engaged. Another alignment tab 98 extends from the top surface 86 for alignment with the slotted hole 72 in the top of the case 26. Lead 16 extends vertically from the connector block through the alignment tab 98. The lead will be shorter than generic leads, thus making it more comfortable for the patient. Internal lead connectors (not illustrated) align with and connect to the multicircuit connector pin 74 of FIG. 5.

PIG. 7 illustrates a perspective view of a connector block 100 for use with generic leads or heart wires which is similar in most respects to connector block 36. Opposing end surfaces 101 and 102 and surface 104 are vertical surfaces, while surfaces 106 and 108 are horizontal surfaces. Surface 110 is in oblique alignment with the other surfaces 101-108. Alignment tabs 112 and 114 extend from surfaces 110 and 104, respectively, for alignment with alignment slots 76 and 78 of the case 26. Another alignment tab 116 extends from the top surface 106 for alignment with the slotted hole 72 in the top of the case 26. Leads 118 and 120 extend upwardly through the alignment tab 116 and through a strain relief 122 for connection to generic pacing leads or heart wires. Connector conducting sleeves 124 and 126 attach electrically to the leads 118 and 120 and include orifices 128 and 130 for accommodation of generic lead pins or heart wires. By way of example and for purposes of illustration only and not to be construed as limiting of the present invention, knurled head screws 132 and 134 clamp the generic lead pins inside the connector sleeves 124 and 126. Finger grips and a colored area or graphics can also be provided for the connector block.

MODE OF OPERATION

When the temporary pacemaker of the present invention is to be used, a disposable lead that is a special accessory is introduced transcutaneously into the heart of the patient or a heart wire is connected to the heart through the chest wall. The wearable temporary pacemaker unit 14 of the present invention is strapped onto the patient's upper arm, chest or another part of the body, using a disposable strap with a convenient fastening device and the connector end of the lead is plugged into a jack of the waterproof unit.

Using the separate remote-control programming unit of the present invention, a medical person communicates with the wearable temporary pacemaker 14 by means of IR radiation, hand-holding the programming unit 12 close to the other temporary pacemaker 14, but not touching it. A compact control panel 22 on the remote programming unit 12 with dedicated buttons can be used to set the desired pulse rate, and other relevant variables, with the results of changes being read from the display that is part of the wearable temporary pacemaker 14 and that is in permanent operation. The remote programming unit 12 is then placed in a safe, but convenient storage location that is inaccessible to the patient and visitors to the patient's room.

After use by one patient, the wearable temporary pacemaker 14 is sterilized by means of liquid disinfectants and/or gas sterilization, and is then ready for use by another patient. The remote programming unit 12 has no need for such treatment since it does not touch the patient and poses no risk in any case; it requires only normal protection from its environment, as would any other electronic unit. For the sake of battery life, the remote programming unit 12 shuts itself off after some specified period (such as 60 minutes) after the last key depression, in case the turn-off step was forgotten.

Various modifications can be made to the present invention with departing from the apparent scope hereof. Communication between the pacemaker and programmer can also be by way of radio frequency signals in lieu of IR signals.

I claim:

1. A remotely programmable temporary pacemaker system for a patient, said pacemaker system comprising;
   a. a sealed external pacemaker having coupling means for removably attaching said pacemaker externally to the body of said patient;
   b. lead means coupled to said pacemaker for providing percutaneous electrical communication between the heart of said patient and said externally attached pacemaker, wherein said lead means comprises a jack, and wherein said lead means is coupled to said pacemaker by means of a custom connector on said pacemaker configured to receive said jack; and
   c. remote programming means for altering pacing parameters of said pacemaker.

2. A remotely programmable temporary pacemaker system for a patient, said pacemaker system comprising:
   a. a sealed external pacemaker having coupling means for removably attaching said pacemaker externally to the body of said patient wherein said pacemaker is sufficiently sealed to allow for sterilization by liquid immersion;
   b. lead means coupled to said pacemaker for providing percutaneous electrical communication between the heart of said patient and said externally attached pacemaker; and
   c. remote programming means for altering pacing parameters of said pacemaker.

3. A remotely programmable temporary pacemaker system for a patient, said pacemaker system comprising:
   a. a sealed external pacemaker having coupling means for removably attaching said pacemaker externally to the body of said patient;
   b. lead means coupled to said pacemkaer for providing percutaneous electrical communication between the heart of said patient and said externally attached pacemkaer;
   c. remote programming means for altering pacing parameters of said pacemaker; and
   d. means to display continuously values of the pacing parameters that were most recently set.

4. The temporary pacemaker system of claim 3 including means to display continuously values of the pacing parameters that were most recently set.

5. The temporary pacemaker system of claim 3 including means to display continuously battery-condition indication.

6. A remotely programmable temporary pacemaker system for a patient, said pacemaker system comprising;
   a. a sealed external pacemaker having coupling means for removably attaching said pacemaker externally to the body of said patient;
   b. lead means coupled to said pacemaker for providing percutaneous electrical communication between the heart of said patient and said externally attached pacemaker;
   c. remote programming means for altering pacing parameters of said pacemaker, wherein said remote programming means comprises a hand-held programming unit comprising an LCD display for presenting parameters and values, and a keyboard with dedicated keys for setting each pacing variable.

7. The temporary pacemaker system of claim 6, wherein said remote programming means communicates with the pacemaker by means of infrared radiation.

8. The temporary pacemaker system of claim 6, wherein said remote programming means communicates with the pacemaker by means of radio-frequency radiation.

9. The temporary pacemaker system of claim 6, wherein said remote programming means communicates with the pacemaker by means of visible radiation.

10. The temporary pacemaker system of claim 6, wherein said remote programming comprises an automatic shut-off means to conserve battery life.

11. A remotely programmable temporary pacemaker system for a patient, said pacemaker system comprising:
    a. a sealed external pacemaker having coupling means for removably attaching said pacemaker externally to the body of said patient;
    b. lead means coupled to said pacemaker for providing percutaneous electrical communication between the heart of said patient and said externally attached pacemaker; wherein said lead means comprises a jack, and wherein said lead means is coupled to said pacemaker by means of a custom connector on said pacemaker configured to receive said jack; and
    c. remote programming means for altering pacing parameters of said pacemaker, wherein said pacemaker has a face with a communication means for communicating with said remote programming means, and means for accepting a pacing lead connector block for connecting said lead means to said pacemaker, said pacing lead connector block including means for engaging into said pacemaker in a specific geometrical relationship.

* * * * *